US00PP26585P2

(12) United States Plant Patent
Uebelhart

(10) Patent No.: US PP26,585 P2
(45) Date of Patent: Apr. 5, 2016

(54) ***PHYSALIS* PLANT NAMED 'PRINCE'**

(50) Latin Name: *Physalis alkekengi*
Varietal Denomination: Prince

(71) Applicant: Georg Uebelhart, Schwarmstedt (DE)

(72) Inventor: Georg Uebelhart, Schwarmstedt (DE)

(73) Assignee: JeLitto Staudensamen GbmH, Schwarmstedt (DE)

( * ) Notice: Subject to any disclaimer, the term of this patent is extended or adjusted under 35 U.S.C. 154(b) by 85 days.

(21) Appl. No.: 13/987,820

(22) Filed: Sep. 7, 2013

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Keith Robinson
(74) *Attorney, Agent, or Firm* — C. A. Whealy

(57) ABSTRACT

A new and distinct cultivar of *Physalis* plant named 'Prince' characterized by its upright and outwardly spreading plant habit; freely branching habit; freely and continuous flowering habit; and large showy orange-colored "lanterns".

2 Drawing Sheets

Botanical designation: *Physalis alkekengi.*
Cultivar denomination: 'PRINCE'.

BACKGROUND OF THE INVENTION

The present invention relates to a new and distinct cultivar of *Physalis* plant, botanically known as *Physalis alkekengi*, commonly known as Winter Cherry, Chinese Lantern or Japanese Lantern Plant and hereinafter referred to by the name 'Prince'.

The new *Physalis* is a product of a planned breeding program conducted by the Inventor in Boijl, The Netherlands. The objective of the breeding program is to create new medium-sized *Physalis* plants with freely and continuous flowering habit that produce large and showy orange-colored "lanterns".

The new *Physalis* plant originated from a cross-pollination conducted by the Inventor in Boijl, The Netherlands during the summer of 2009 of a proprietary selection of *Physalis alkekengi* identified as code name JEL12-17, not patented, as the female, or seed, parent with a proprietary selection of *Physalis alkekengi* identified as code name JEL03, not patented, as the male, or pollen, parent. The new *Physalis* was discovered and selected by the Inventor as a single flowering plant from within the progeny of the stated cross-pollination in a controlled environment in Boijl, The Netherlands in October, 2010.

Asexual reproduction of the new *Physalis* plant by terminal cuttings in Boijl, The Netherlands since July, 2011 has shown that the unique features of this new *Physalis* plant are stable and reproduced true to type in successive generations.

SUMMARY OF THE INVENTION

Plants of the new *Physalis* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Prince'. These characteristics in combination distinguish 'Prince' as a new and distinct *Physalis* plant:

1. Upright and outwardly spreading plant habit.
2. Freely branching habit.
3. Freely and continuous flowering habit.
4. Large showy orange-colored "lanterns".

Plants of the new *Physalis* differ from plants of the female parent selection in the following characteristics:

1. Plants of the new *Physalis* are more compact than plants of the female parent selection.
2. Plants of the new *Physalis* flower more continuously than plants of the female parent selection.

Plants of the new *Physalis* differ from plants of the male parent selection in the following characteristics:

1. Plants of the new *Physalis* are larger than plants of the male parent selection.
2. Plants of the new *Physalis* are more freely flowering than plants of the male parent selection.
3. Plants of the new *Physalis* produce larger "lanterns" than plants of the male parent selection.

Plants of the new *Physalis* can be compared to plants of *Physalis alkekengi* 'King', disclosed in U.S. Plant Pat. No. 22,579. In side-by-side comparisons conducted in Boijl, The Netherlands, plants of the new *Physalis* differed primarily from plants of 'King' in the following characteristics:

1. Plants of the new *Physalis* were more outwardly spreading and broader than plants of 'King'.
2. Leaves of plants of the new *Physalis* were larger, slightly lighter green in color and more lobed than leaves of plants of 'King'.
3. Plants of the new *Physalis* produced larger "lanterns" than plants of 'King'.

BRIEF DESCRIPTION OF THE PHOTOGRAPHS

The accompanying colored photographs illustrate the overall appearance of the new *Physalis* plant showing the colors as true as it is reasonably possible to obtain in colored reproductions of this type. Colors in the photographs may differ slightly from the color values cited in the detailed botanical description which accurately describe the colors of the new *Physalis* plant.

The photograph on the first sheet is a side perspective view of a typical flowering plant of 'Prince' grown in a container.

The photograph on the second sheet is a close-up view of typical plant of 'Prince' with developing and fully developed "lanterns".

DETAILED BOTANICAL DESCRIPTION

Plants used for the aforementioned photographs and following description were grown during the summer and autumn in an outdoor nursery in Boijl, The Netherlands and under cultural practices typical of commercial *Physalis* production. Plants used for the photographs were grown in three-liter containers and plants used for the description were grown in ground beds. During the production of the plants, day temperatures ranged from 15° C. to 25° C. and night temperatures ranged from 10° C. to 15° C. Plants were one year old when the photographs and description were taken. In the following description, color references are made to The Royal Horticultural Society Colour Chart, 2001 Edition, except where general terms of ordinary dictionary significance are used.

Botanical classification: *Physalis alkekengi* 'Prince'.

Parentage:

*Female parent*.—Proprietary selection of *Physalis alkekengi* identified as code name JEL12-17, not patented.

*Male parent*.—Proprietary selection of *Physalis alkekengi* identified as code name JEL03, not patented.

Propagation:

*Type*.—By terminal cuttings.

*Time to initiate roots, summer*.—About three weeks at 15° C. to 20° C.

*Time to produce a rooted young plant, summer*.—About five weeks at 15° C. to 20° C.

*Root description*.—Medium in thickness, fibrous; plants produce fibrous rhizomes; color, closest to 158C.

*Rooting habit*.—Freely branching; medium density.

Plant description:

*Plant and growth habit*.—Herbaceous perennial; upright and outwardly spreading plant habit; freely branching habit with about three to four basal branches developing per plant; moderately vigorous growth habit.

*Plant height*.—About 15 cm to 20 cm.

*Plant width*.—About 35 cm to 45 cm.

*Basal branch description*.—Aspect: Upright to drooping. Internode length: About 2 cm to 3 cm. Strength: Moderately strong. Texture: Pubescent; no prickles. Color: Close to 144A.

Leaf description:

*Arrangement*.—Alternate and opposite, simple.

*Length*.—About 6 cm to 8 cm.

*Width*.—About 3 cm to 5 cm.

*Shape*.—Deltoid to ovate.

*Apex*.—Acute to acuminate.

*Base*.—Obtuse to truncate.

*Margin*.—Lobed.

*Texture, upper and lower surfaces*.—Pubescent.

*Luster, upper surface*.—Slightly glossy.

*Luster, lower surface*.—Matte.

*Venation pattern*.—Pinnate.

*Color*.—Developing and fully developed leaves, upper surface: Close to 137A; venation, close to 147C. Developing and fully developed leaves, lower surface: Close to 146B; venation, close to 147C.

*Petioles*.—Length: About 2 cm. Diameter: About 2 mm. Texture, upper and lower surfaces: Smooth. Color, upper and lower surfaces: Close to 144A.

Flower description:

*Flower arrangement and shape*.—Single round axillary flowers; flowers face mostly outwardly; freely flowering habit with more than 50 flowers developing per plant throughout the flowering season.

*Natural flowering season*.—Plants begin flowering about eight to ten weeks after planting; in the garden, flowering continuous from June to November The Netherlands.

*Flower longevity on the plant*.—About one week; "lanterns" persist throughout the flowering season.

*Fragrance*.—None detected.

*Flower buds*.—Length: About 4 mm to 6 mm. Diameter: About 2 mm to 3 mm. Shape: Oval to obovate. Texture: Smooth, pubescent. Color: Close to 141D.

*Flower diameter*.—About 1 cm.

*Flower length (height)*.—About 1 cm.

*Petals*.—Arrangement: Five in a single whorl. Length: About 7 mm. Width: About 5 mm. Shape: Obovate. Apex: Acute to acuminate. Base: Cordate. Margin: Entire. Texture, upper and lower surfaces: Smooth. Color: When opening, upper and lower surfaces: Close to 155B. Fully opened, upper and lower surfaces: Close to 155B.

*Calyx*.—Arrangement: Five sepals in a single whorl; fused, forming a nearly globose-shaped structure also referred to as a "lantern". Lantern height: About 7.5 cm to 8.5 cm. Lantern diameter: About 3.5 cm to 4.5 cm. Sepal shape: Ovate. Sepal apex: Cuspidate. Sepal base: Obtuse, peltate. Sepal margin: Entire. Sepal texture, upper and lower surfaces: Papery; rugose. Sepal color, fully developed, upper surface: Close to 33B. Sepal color, fully developed, lower surface: Close to 32B.

*Peduncles*.—Length: About 3 cm. Diameter: About 3 mm. Aspect: Drooping to about 90° from stem axis. Strength: Strong, flexible. Texture: Smooth. Color: Close to 144A becoming closer to 33B.

*Reproductive organs*.—Stamens: Quantity per flower: Four. Filament length: About 1 mm. Filament color: Close to 155D. Anther length: About 1 mm to 2 mm. Anther shape: Lanceolate to elliptic. Anther color: Close to 155D. Pollen amount: Not observed. Pistils: Quantity per flower: One. Pistil length: About 3 mm. Stigma shape: Round. Stigma color: Close to 155D. Style length: About 2 mm. Style color: Close to 155D. Ovary color: Close to 145D.

*Fruits*.—Type: Berry. Shape: Globose. Length: About 2.5 cm. Diameter: About 2.5 cm. Weight: About 10 gr. Texture: Smooth, glabrous. Venation: Medium. Luster: Very glossy. Firmness: Medium. Color: Close to 33B.

*Seeds*.—Length: About 3 mm. Diameter: About 2 mm. Color: Close to 159B.

Disease & pest resistance: Plants of the new *Physalis* have not been observed to be resistant to pathogens and pests common to *Physalis* plants.

Temperature tolerance: Plants of the new *Physalis* have been observed to tolerate temperatures ranging from about −30° C. to about 35° C.

It is claimed:

1. A new and distinct *Physalis* plant named 'Prince' as illustrated and described.

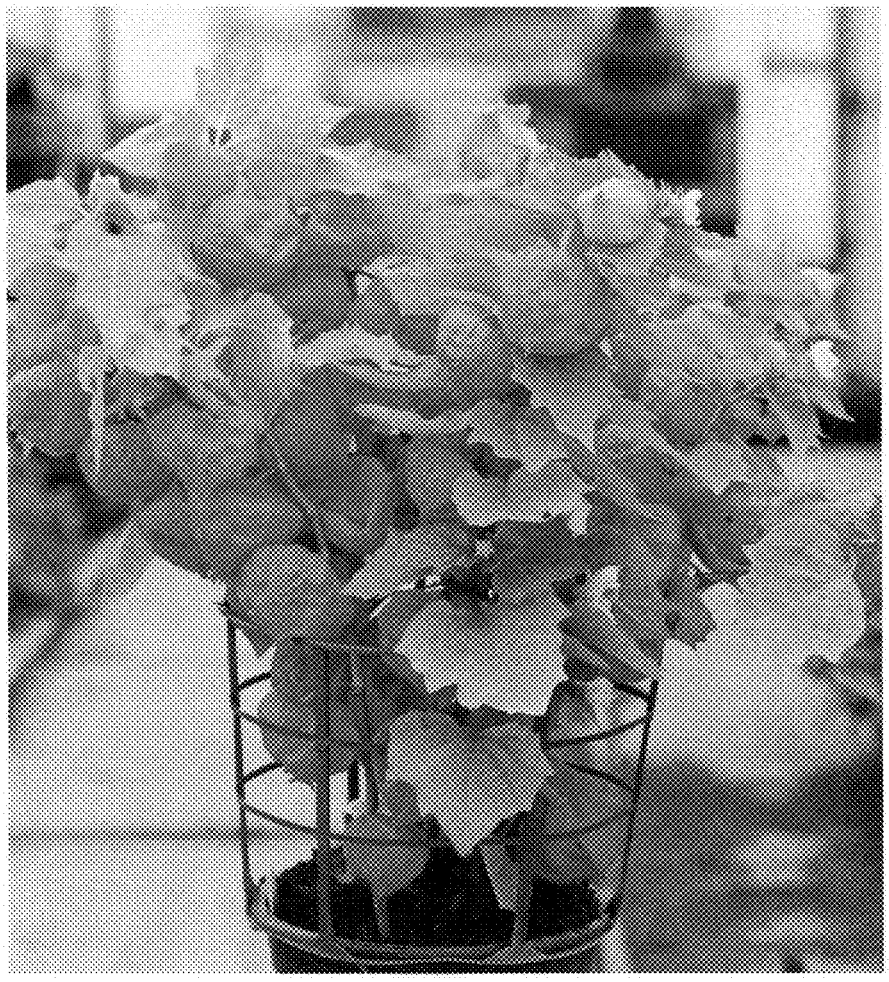

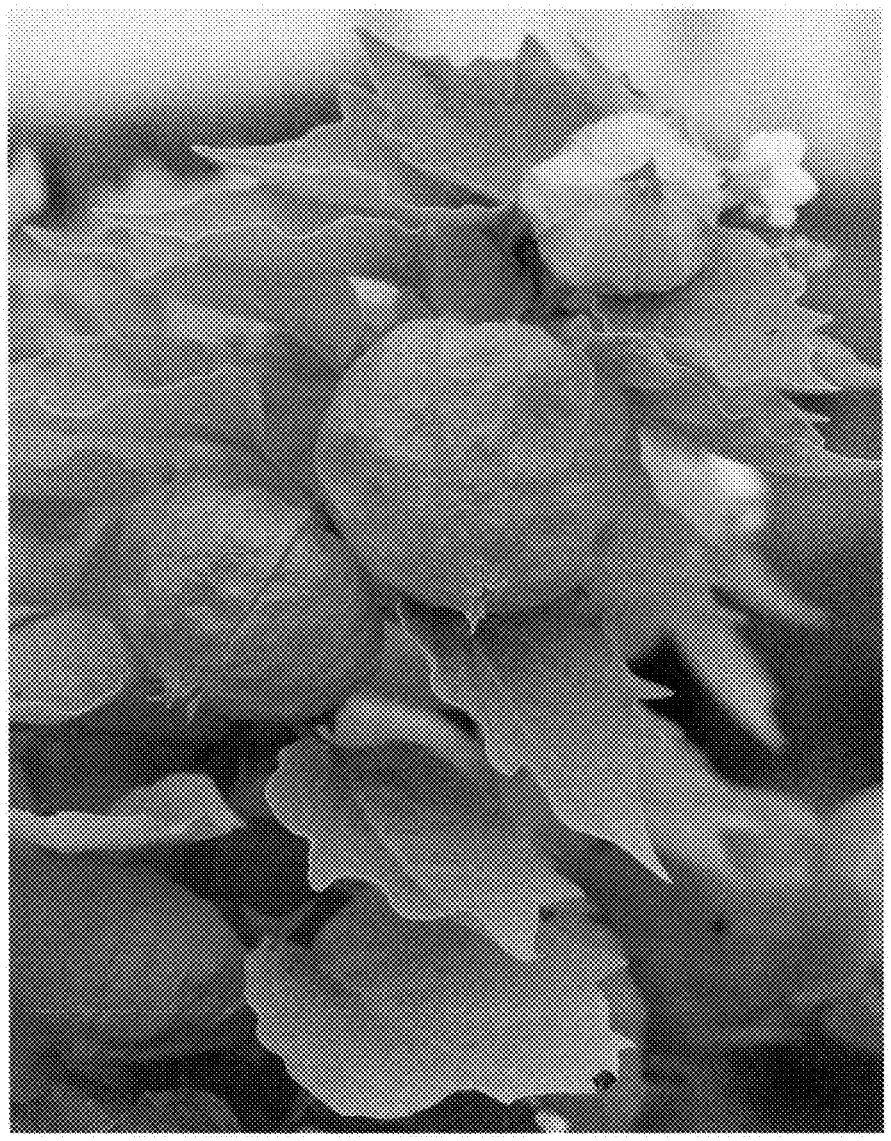

* * * * *